United States Patent
Braun et al.

(10) Patent No.: US 10,166,124 B2
(45) Date of Patent: Jan. 1, 2019

(54) ORTHOSIS CONTROL

(71) Applicant: OTTO BOCK HEALTHCARE GMBH, Duderstadt (DE)

(72) Inventors: Jan-Matthias Braun, Gottingen (DE); Florentin Worgotter, Gottingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 832 days.

(21) Appl. No.: 14/419,165

(22) PCT Filed: Jul. 19, 2013

(86) PCT No.: PCT/EP2013/065285
§ 371 (c)(1),
(2) Date: Feb. 2, 2015

(87) PCT Pub. No.: WO2014/019872
PCT Pub. Date: Feb. 6, 2014

(65) Prior Publication Data
US 2015/0190250 A1    Jul. 9, 2015

(30) Foreign Application Priority Data

Aug. 2, 2012    (DE) .................. 10 2012 107 117

(51) Int. Cl.
*A61F 2/72*    (2006.01)
*A61F 2/60*    (2006.01)
(Continued)

(52) U.S. Cl.
CPC .................. *A61F 2/72* (2013.01); *A61F 2/60* (2013.01); *A61F 2/66* (2013.01); *B25J 9/0006* (2013.01);
(Continued)

(58) Field of Classification Search
CPC ...... A61F 2/72; A61F 2/66; A61F 2/60; A61F 2002/7635; A61F 2002/764;
(Continued)

(56) References Cited

U.S. PATENT DOCUMENTS

| 6,755,870 | B1 | 6/2004 | Biedermann et al. |
| 7,713,217 | B2 * | 5/2010 | Ikeuchi .................. A61H 3/008 600/587 |

(Continued)

FOREIGN PATENT DOCUMENTS

| CN | 101316565 | 12/2008 |
| CN | 101437470 | 5/2009 |

(Continued)

OTHER PUBLICATIONS

Prentice, S.D., et al., "Simple artificial neural network models can generate basic muscle activity patterns for human locomotion at different speeds," Exp. Brain Res., vol. 123, Issue 4, pp. 474-480, Nov. 1998.

(Continued)

*Primary Examiner* — Quang D Thanh
(74) *Attorney, Agent, or Firm* — Holland & Hart

(57) ABSTRACT

In order to control at least one adjustable actuator of a connection apparatus to an orthopedic device with tower limbs, actual values of at least two movement parameters of the orthopedic device are continuously acquired by at least two sensors. A functional relationship is established between the sequences of actual values of the at least two movement parameters. This functional relationship is continuously repeatedly compared to functional relationships in the case of defined movement patterns in order to select in each case the movement pattern which fits best to the acquired actual (Continued)

values. Then control signals for the actuator are generated using a sequence of intended values defined for the best-fitting movement pattern.

21 Claims, 5 Drawing Sheets

(51) Int. Cl.
*A61F 2/66* (2006.01)
*B25J 9/00* (2006.01)
*A61F 2/50* (2006.01)
*A61F 2/70* (2006.01)
*A61F 2/76* (2006.01)

(52) U.S. Cl.
CPC . *A61F 2002/5003* (2013.01); *A61F 2002/701* (2013.01); *A61F 2002/764* (2013.01); *A61F 2002/7615* (2013.01); *A61F 2002/7625* (2013.01); *A61F 2002/7635* (2013.01); *A61F 2002/7665* (2013.01)

(58) Field of Classification Search
CPC ........ A61F 2002/7615; A61F 2002/701; A61F 2002/5003; A61F 2002/7665; A61F 2002/7625; B25J 9/0006; A61H 1/00; A61H 1/0237; A61H 1/024; A61H 1/0244; A61H 1/0262; A61H 1/0266; A61H 2201/5069; A61H 2201/5071; A61H 2205/088; A61H 2205/10; A61H 2205/102; A61H 2205/106; A61H 2205/108; A61H 2205/12; A61H 3/00
See application file for complete search history.

(56) References Cited

U.S. PATENT DOCUMENTS

| | | |
|---|---|---|
| 7,896,927 B2 | 3/2011 | Clausen et al. |
| 8,048,172 B2 | 11/2011 | Jonsson et al. |
| 8,057,550 B2 | 11/2011 | Clausen et al. |
| 2002/0052663 A1 | 5/2002 | Herr et al. |
| 2006/0276728 A1* | 12/2006 | Ashihara ............... A61F 5/0102 601/5 |
| 2007/0123997 A1* | 5/2007 | Herr .......................... A61F 2/60 623/27 |
| 2009/0054996 A1 | 2/2009 | Sykes et al. |
| 2010/0094185 A1* | 4/2010 | Amundson ........... A61F 5/0102 602/16 |
| 2010/0305716 A1 | 12/2010 | Pusch et al. |
| 2011/0071452 A1 | 3/2011 | Auberger |
| 2012/0016278 A1* | 1/2012 | Nakashima ............ A61H 1/024 601/34 |
| 2012/0226364 A1 | 9/2012 | Kampas et al. |

FOREIGN PATENT DOCUMENTS

| | | |
|---|---|---|
| CN | 102036626 | 4/2011 |
| CN | 102202613 | 9/2011 |
| DE | 19521464 A1 | 3/1997 |
| DE | 60131377 T2 | 9/2008 |
| DE | 102007053389 A1 | 5/2009 |
| DE | 102008024748 A1 | 12/2009 |
| DE | 102009052887 A1 | 5/2011 |
| EP | 0628296 A2 | 12/1994 |
| EP | 1058524 A1 | 12/2000 |
| EP | 1442703 A2 | 8/2004 |
| EP | 1531767 B1 | 12/2008 |
| WO | 2006024876 A2 | 3/2006 |
| WO | 2010027968 | 3/2010 |

OTHER PUBLICATIONS

PCT International Search Report for PCT International Patent Application No. PCT/EP2013/065285, dated Oct. 24, 2013.

* cited by examiner

ORTHOSIS CONTROL

TECHNICAL FIELD

The invention relates to a method for controlling at least one adjustable actuator of an orthopedic device including connection apparatuses to a lower limb. Furthermore, the present invention relates to an orthopedic device comprising connection apparatuses for connection to a lower limb and comprising a control apparatus actuating an actuator.

BACKGROUND

The orthopedic device is, in particular, a so-called orthosis, i.e. a device which supports a limb that is present. However, in principle, the orthopedic device can also be a so-called prosthesis, which at least partly replaces a limb.

Here, an actuator of an orthopedic device should be understood to mean any means which influences a relative movement between parts of the orthopedic device. This influencing may be passive, such as in the case of e.g. a damper, or else active, such as in the case of e.g. a motor.

If the term "movement pattern" is used in the following, it in particular includes the meaning of a "gait"; however, it is not restricted thereto, even in the case of a lower limb.

In the case of an unchanging movement pattern, for example when walking in a plane or when climbing stairs, which is carried out continuously, it is comparatively easy to set the actuator of an orthopedic device in a manner that fits. However, when the movement pattern changes, there needs to be an adjustment to a different setting of the actuator. This adjustment can be undertaken manually by the user of the orthopedic device or it can be triggered by means of a specific movement of the orthopedic device. However, a precondition for a movement with the orthopedic device that is as unimpeded as possible for the user is that the orthopedic device adapts the actuator or actuators thereof independently to the current movement pattern. To this end, various suggestions have already been proposed.

A leg prosthesis with an artificial knee joint and a method for controlling a leg prosthesis are known from EP 1 058 524 B1. The leg prosthesis includes a thigh part, a below-knee part and a knee joint connecting the two. The knee joint comprises a damping element for controlling the knee joint movement. An apparatus registers the knee angle and a further apparatus registers the force acting on the prosthesis. A controller for controlling the damping element as a function of the registered values for the knee angle and for the force is regulated in accordance with the gait of the wearer of the leg prosthesis. Here, the controller is embodied in such a way that it controls the damping element as a function of control parameters for various gait speeds stored in advance. These parameters are corrected within the scope of regulating the control as a function of the gait. To this end, a control parameter is selected from the stored control parameters as a function of the registered values for the knee angle and for the force. The selected control parameter is then modified to a value as a function of the registered values for the knee angle and for the force, which value equals, or is different from, the previously stored value. This modified control parameter is then stored in place of the selected control parameter. This regulation sets in when established actual step values deviate from predetermined intended step values which are the same for each prosthesis wearer. By way of example, these include a maximum bend angle and a lead-in time, which is the time between an extension limit and touchdown of the heel within a step. In this manner, the control of the damping element is adapted to the respective prosthesis wearer.

EP 1 531 767 B1 has disclosed a control apparatus and a method for controlling a prosthesis comprising an actuator. This includes a method for determining a locomotion portion and a locomotion phase portion in order to be able to control the prosthesis in real time. This method comprises the provision of a plurality of main artificial proprioceptors, the reception of a data signal from each one of the main artificial proprioceptors, the obtainment of a first and a second derivative signal from the data signals, the obtainment of a third derivative signal for at least some of the data signals and the use of a set of first state machines in order to select a state from a multiplicity of possible states for each main artificial proprioceptor with the corresponding data and derivative signals. Furthermore, the locomotion phase portion is generated using the states of the main artificial proprioceptors; and a second state machine is used to select the locomotion portion using results which are assigned to the data signals from a plurality of possible locomotion portions. That is to say, the locomotion portion and the locomotion phase portion, i.e. movement state and phase, are identified in addition to the current values of the main artificial proprioceptors by various derivatives of said values and are linked to specific commands for the actuator of the prosthesis. To this end, the signals from the main proprioceptors or the derivatives thereof are compared to entries in comparison value tables and, to the extent that a correspondence is present, the actuators are actuated by actuation commands linked to these entries in the comparison value tables. Here, the entries in the comparison value tables are fixed, i.e. not adapted to the individual prosthesis wearer.

DE 10 2007 053 389 A1 has disclosed a method for controlling an orthopedic joint of a lower extremity in at least one degree of freedom using an adjustable actuator which, for the purposes of adapting an orthopedic device, which includes top-side connection means to a limb and an orthopedic joint arranged in a hinged manner distally from the connection means, serves walking situations that deviate from walking in the plane. In this known method, a plurality of parameters of the orthopedic device are registered by means of sensors. The registered parameters are compared to criteria which were generated on the basis of a plurality of parameters and/or parameter profiles and which are stored in a computer unit. A criterion suitable on the basis of the established parameters and/or parameter profiles is selected, and movement resistors, scopes of movement, drive forces and/or the profiles thereof are adapted as a function of the selected criterion in order to control extra functions.

DE 10 2008 024 748 A1 has disclosed a knee orthosis and a method for controlling a knee orthosis. The method for controlling the knee orthosis, which includes a thigh structure, a joint apparatus and a below-knee structure comprising a foot part, provides for an effective torque, in particular an ankle element, to be determined within the orthosis and for the resistance of the actuator unit to be modified as a function of the torque. In a complementary manner, the actuator unit can be modified as a function of a knee torque, the knee angle or the spatial orientation of at least one thigh structure or below-knee structure. As a result, it is possible to provide control of the standing and swing phase in the case of patients with paralysis, who can no longer control their leg as desired. The section modulus, which, for example, can be modified by means of a hydraulic actuator, renders it possible to generate a knee torque in such a way that standing phase flexion and alternating downward walking and walking downstairs are made possible. An appropriate support of the movement should be brought about by means of active actuator units.

DE 10 2009 052 887 A1 has disclosed a method for controlling an orthotic or prosthetic joint of a lower extremity. The joint includes a resistance apparatus, to which at least one actuator is assigned, by means of which the bending and/or extension resistance is modified as a function of sensor data. Sensors provide state information during the use of the joint. The sensor data are established by at least one apparatus for registering at least two torques or a torque and a force. The sensor data of at least two variables established thus are linked to one another by a mathematical operation. As a result, at least one auxiliary variable is calculated, on which the control of the bending and/or extension resistance is based.

A method for controlling at least one adjustable actuator of an orthopedic device including connection apparatuses to a lower limb, and a corresponding orthopedic device comprising connection apparatuses to a lower limb, an adjustable actuator, at least two sensors, which continuously register actual values of at least two movement parameters of the orthopedic device, and a control apparatus which analyzes the registered values and sets the actuator using control signals on the basis thereof, which orthopedic device components are known from DE 195 21 464 A1. This relates specifically to the control of the knee brake of a prosthetic knee joint of a thigh prosthesis. Here, a computer controlled braking torque is modified continuously between "free" and "blocked" as a function of the gait movement of the prosthesis wearer and the gait movement is characterized in the form of measurement data by measured EMG values, pressure values measured in the region of the foot, by the respective knee angle and the respective angular speed measured between prosthesis thigh part and below-knee part. For the purposes of improved adaptation of the knee braking control to various natural gaits, the respective gait is established from a number of predetermined gaits, established in advance for the respective prosthesis wearer, by evaluating at least some of the measurement data. Then, a control program assigned to this established gait is selected. A step period, defined as a period of time between two successive heel/floor contacts subdivided into a plurality of phases is set for each control program, the respective endpoint of which is determined by measurement data that is predetermined for this phase and transmitted in each case. Specific brake values which are applied to the knee brake and which possibly change during this phase are assigned to each phase. The respective carried out gait is established by comparing the transmitted measurement data with reference data predetermined for each gait. Here, it is intended to be expedient to establish the reference data from the EMG data measured for each individual gait. Basing the establishment of the respectively carried out gait on EMG data requires the reproducible measurement thereof. However, recording EMG data is not at all possible in the case of some patient groups. Moreover, establishing the gaits by data comparison is complicated and susceptible to errors. The known method and the corresponding thigh prosthesis have therefore not found widespread use in practice.

S. D. Prentice et al.: Simple artificial neuron network models can generate basic muscle activity patterns for human locomotion at different speeds, Exp. Brain Res (1998) 123:474-480 has disclosed the practice of representing muscle activation patterns when walking with the aid of an artificial neural network on the basis of a sine function and a cosine function with a period length equal to the duration of a step.

DE 601 31 377 T2 has disclosed a speed-adapted and patient-adapted control scheme for a knee prosthesis to carry out a method for controlling at least one adjustable actuator of an orthopedic device including connection apparatuses to a lower limb. The control scheme is provided for controlling a standing phase damping of the knee prosthesis worn by a patient. Correlations in respect of sensor data and the standing phase damping are stored in a memory of the knee prosthesis. These correlations are set on the basis of clinical tests of amputees with different body sizes and characterize the knee behavior when the foot prosthesis is in contact with the floor. Sensor information is used in conjunction with these correlations in order to define how the standing phase damping is intended to be modulated when standing, walking or running.

US 2009/0054996 A1 has disclosed a knee prosthesis which includes an adjustable joint movement control unit for automatically controlling the joint. An electronic memory unit stores a target relationship between a kinetic or kinematic movement parameter and the walking speed. The target relationship defines a number of values of the movement parameter, which are respectively connected to a different walking speed. A monitoring system generates monitoring signals that reproduce the walking speed values and values of the movement parameter, as occur at different walking speeds. An adaptation system automatically adapts the joint movement control unit if the monitoring signals show a deviation from the target relationship in order to bring the movement parameter back into the range of a value defined by the target relationship for the respective walking speed.

SUMMARY

The invention is based on the object of highlighting a method for controlling at least one adjustable actuator of an orthopedic device and an orthopedic device, which reliably identify the respective movement pattern on the basis of movement parameters that are easy to measure.

The object of the invention is achieved by a method for controlling at least one adjustable actuator of an orthopedic device, and by an orthopedic device comprising an adjustable actuator and a control apparatus.

In a method according to the invention for controlling at least one adjustable actuator of an orthopedic device including connection apparatuses to a lower limb, actual values of at least two movement parameters of the orthopedic device are continuously registered using at least two sensors. A functional relationship is established between the sequences of the actual values of the at least two movement parameters. That is to say, the functional relationship between the sequence of the actual values of the one of the at least two parameters and the sequence of the actual values of the other one thereof is established. The functional relationship thus specifies the relative relationship between these two and all further considered sequences of actual values of movement parameters. This functional relationship is compared in a continuously repeating manner to functional relationships in the case of defined movement patterns in order respectively to select the movement pattern fitting best to the registered actual values. Then control signals for the actuator are generated using a sequence of intended values defined for the best-fitting movement pattern.

Specific relationships between the various movement parameters that can be registered by sensors at an orthopedic device can be highlighted in the case of almost all movement patterns. According to the invention, these relationships are registered as functional relationships between the actual values of at least and preferably two such movement parameters. In the case of a suitable selection of the movement parameters, these functional relationships of the actual values thereof are characteristic for each relevant movement pattern, i.e. the best-fitting one of these movement patterns can be selected in a comparatively simple way as the currently valid one by comparing the current functional relationship to the functional relationships of defined movement patterns. In particular, no time scaling, i.e. no adaptation to a current step speed, is required therefor. If control signals for the actuator are then generated using a sequence of intended values defined for this best-fitting movement pattern, the resulting settings of the actuator are ideally matched to the current movement pattern of the orthopedic device or of the wearer thereof.

In the step of establishing the functional relationship, it is possible to specifically establish a function which maps the sequence of the actual values of the one of the at least two movement parameters onto the sequence of the actual values of the other one of the at least two movement parameters. The time profile of this function is then compared to the time profiles of corresponding functions of the defined movement patterns.

There is particular clarity in relation to the functional relationship if the actual values of the at least two movement parameters are represented by a trigonometric function in the step of establishing the functional relationship thereof. Also, the comparison of this trigonometric function to those of the defined movement patterns for selecting the best-fitting movement pattern is easily comprehensible and, moreover, easy to carry out using known algorithms such as e.g. that of the least square error. The representation as a trigonometric function requires two movement parameters, the actual values of which move back and forth between two limit values with an approximately 90° phase offset, if there should not be a preceding transformation of the actual values of at least one of the two parameters. However, such movement parameters are, in particular, registrable using angle sensors at the orthopedic device. Specifically, the two movement parameters can be a hip angle and a knee angle, which are measured at the orthopedic device.

Within the step of generating control signals for the actuator, the sequence of the intended values, which are predetermined by the respective best-fitting established movement pattern, is output as a function of the sequence of the actual values of at least one of the at least two movement parameters. In this manner, the sequence of the intended values is synchronized to the phase of the actual movement. If the actual values of the two movement parameters are represented as a trigonometric function, the sequence of the intended values can, in particular, be output as a function of the angle about the origin of the trigonometric function at which the actual values of both movement parameters are currently to be found. In this embodiment of the method according to the invention, no explicit timescale or adaptation to current step lengths is required when using the intended values. Rather, all adaptations required in this direction are brought about implicitly, by virtue of e.g. a faster advance of the movement phase resulting in an acceleration of the sequence of the intended values.

Alternatively or additionally, the sequence can be synchronized in time, i.e. put into relation with a specific movement point, with the aid of the signal of a further sensor. This measure may be sufficient for outputting the control signals to the actuator with a correct phase. In particular, the further sensor can be a foot or heel pressure sensor, which independently registers the floor contact of the foot of the user or of the orthopedic device.

When carrying out the method according to the invention, it is not necessary to always await full movement cycles and corresponding circulations of an employed trigonometric function in order to seek for a possibly better fitting, new movement pattern. Rather, the selection of a new defined movement pattern, which has a better fit to the current sequence of the actual values of the movement parameters or to the functional relationship thereof, can be started immediately as soon as a deviation between the current functional relationship of the actual values of the movement parameters and the functional relationship in the case of the movement pattern previously established as being the best-fitting one indicates that the wearer of the orthopedic apparatus has initiated a new movement pattern. The selection of a new movement pattern resulting therefrom is to be updated continuously until it has stabilized. If the actuation is already set dependent on a movement pattern selected at such an early stage, there is a high probability of it already being set in an ideal manner from a very early time. By contrast, the risk of said actuator being set in a completely unfitting manner as a result of a movement pattern selected incorrectly on the basis of an initially small value base is only very small.

In a preferred embodiment of the method according to the invention, a deviation of the actual values of the one of the at least two movement parameters from expected values, which are predetermined by the actual values of the other one of the at least two movement parameters and the most recently established functional relationship between the sequences of the actual values of the at least two movement parameters, is classified as a movement error if this deviation has a duration below a predetermined duration limit and/or the values during the deviation do not fit to any one of the defined movement patterns within a predetermined error limit. Here, it is also possible to consider an integral or sum of the deviations, determined at fixed intervals, over a period of time.

In principle, it is also possible to consider a frequency spectrum of the deviation, wherein, a movement error is deduced if the deviation has a dominant frequency above a predetermined limit frequency. Here, the frequency of the deviation means, in particular, that the deviation of the actual values of the one movement parameter change from the corresponding expected values at this frequency or the actual values themselves change at this frequency.

Actual values which include a deviation classified as a movement error are not used to seek for a possibly better fitting movement pattern and for an associated sequence of intended values to actuate the actuator. Rather, at least initially, the movement pattern previously selected as best fitting is maintained and monitoring is carried out as to whether the actual values of the at least one movement parameter return to the expected values which are set by the previous movement pattern and the actual values of the other movement parameter. As soon as this is the case, the control signals for the actuator continue to be generated using the sequence of the intended values for the previous movement pattern.

In this embodiment of the method according to the invention, each instance of tripping or stumbling, which interrupts the previous sequence of the actual values of the two movement parameters, is typically identified and counteracted in a practical manner in relation to the actuation of the actuator. To this end, the control signals for the actuator can be set to a predetermined fall-back value while a movement error is present. Such a predetermined fall-back value is no longer dependent on the actual values the two movement parameters. However, it may be dependent on the movement pattern which fitted best up until now and/or on the previous sequence of the actual values. By way of example, if the trip is identified, the damping of a joint of the orthopedic device can be set in a targeted manner to a comparatively high fall-back value.

Furthermore, it is preferable in the case of the method according to the invention if the movement patterns are defined individually for the respective wearer of the orthopedic device. This means that the movement patterns are defined in correspondence with the natural movement patterns of the wearer of the orthopedic device. As a result, an ideal actuation of the actuator of the orthosis should be ensured for, in particular, wearers of orthoses, even in the case of movement patterns which do not correspond to a conventional scheme. Such movement patterns by way of example include those that emerge from sparing an injured body part.

The definitions of the individual movement patterns can be updated on the basis of actual functional relationships between the actual values of the movement parameters assigned thereto. Functional relationships to which a previously defined movement pattern fits best are the current representatives of this movement pattern. In particular, these reflect changes in the movement pattern as, for example, occur regularly over the convalescence process in the case of convalescing wearers of orthoses. Therefore, it is advantageous to include in the definition of the movement pattern the changes, occurring over time, of the functional relationships assigned to a movement pattern.

At least two movement patterns are defined in the method according to the invention. By way of example, these can be the movement patterns assigned to walking in the plane and climbing stairs. However, the movement patterns are preferably also even differentiated beyond this. By way of example, an additional movement pattern can be assigned to quick running or to going down stairs. Individual wearers of an orthopedic device may also be interested in defining specific movement patterns in order e.g. to be able to dance different dances, wherein a movement pattern is defined for each dance, which movement pattern is identified by the method according to the invention by way of the associated functional relationship between the movement parameters and wherein the method then sets the ideal settings of the actuator of the orthopedic device for the respective dance.

Just like the movement patterns, the sequences of the intended values for the defined movement patterns are preferably also set individually for the respective wearer of the orthopedic device in order to provide such wearer with maximum support during the movements wanted by said wearer by way of the control signals, generated by the intended values, for the actuator. This individual definition can be brought about by specialist staff, who are supported by analysis devices. However, certain modifications to the definition can also be undertaken by the wearer of the orthopedic device themselves.

In addition to modifying the definition of the sequences of the intended values for setting the actuator in order to undertake a basic optimization or adaptation to long-term changes in the movement patterns, it is possible, when generating the control signals for the actuator on the basis of the respective sequence of the intended values, to take into account a history of the actual values of at least one of the movement parameters and/or a history of the functional relationship between the sequences of the actual values of the at least two movement parameters. By way of example, shortening step lengths may indicate a tiring of the wearer of the orthopedic device, or at least increasing exertion, which may be counteracted by more support by the orthopedic device.

However, indications of e.g. tiring or exertion of the wearer of the orthopedic device can also be obtained by virtue of at least one state value of the limb being registered by means of at least one state sensor and by virtue of the sequence of intended values defined for the best-fitting movement pattern being adapted, taking into account the registered state values, for setting the actuator.

In addition to state values of the limb, it is also possible to take into account surrounding state values, which describe the state of the surroundings in which the orthopedic device is used, when adapting the sequence of intended values defined for the best-fitting movement pattern for setting the actuator. By way of example, these surrounding state values include the temperature, a coefficient of static friction of the ground or the like.

The derivative of the surrounding gradient, that is to say the change in the gradient of the ground on which the current movement takes place, is of particular interest for an ideal control of the actuator of the orthopedic device. If possible, the derivative of the surrounding gradient can be measured directly in order to adapt the control signals for the actuator. However, since this derivative of the surrounding gradient is also reflected in the registered actual values of the movement parameters of the orthopedic device, it can also be established from the latter.

The control apparatus carries out the method according to the invention in an orthopedic device according to the invention comprising connection apparatuses to a lower limb, comprising an adjustable actuator, comprising at least two sensors which continuously register the actual values of at least two movement parameters of the orthopedic device and comprising a control apparatus which analyzes the registered values and sets the actuator using control signals on the basis thereof. Therefore, all preferred embodiments of the method according to the invention correspond to preferred embodiments of the device according to the invention.

Advantageous developments of the invention emerge from the patent claims, the description and the drawings. The advantages of features and combinations of a plurality of features, specified in the description, are merely exemplary and can be effective in an alternative or cumulative manner, without the advantages of embodiments according to the invention necessarily needing to be obtained. Without this changing the subject matter of the appended patent claims, the following applies in respect of the disclosure of the original application documents and of the patent: further features can be gathered from the drawings—in particular from the depicted geometries and the relative dimensions of a plurality of components in relation to one another as well as from the relative arrangement and functional connection thereof. The combination of features from different embodiments of the invention or of features from different patent claims is likewise possible in a manner deviating from the selected dependency references of the patent claims and is encouraged hereby. This also relates to those features which are depicted in separate drawings or are mentioned in the description thereof. These features may also be combined with features of different patent claims. Likewise, features listed in the patent claims can be dispensed with in further embodiments of the invention.

The features specified in the patent claims and in the description are, in terms of their number, to be understood in such a way that precisely this number, or a greater number than the specified number, is present, without this requiring an explicit use of the phrase "at least". Thus, for example, if reference is made to one step or element, this should be understood to mean that exactly one step or element, two steps or elements, or more steps or elements are present. By contrast, if the precise number of a feature is intended to be specified, use is made of the adverb is "precisely" in front of the respective feature. These features can be complemented by other features or these can be the only features of which the respective method or the respective device consists.

BRIEF DESCRIPTION OF THE DRAWINGS

In the following, the invention is described and explained in more detail on the basis of preferred exemplary embodiments depicted in the figures.

DETAILED DESCRIPTION

Figure 1:
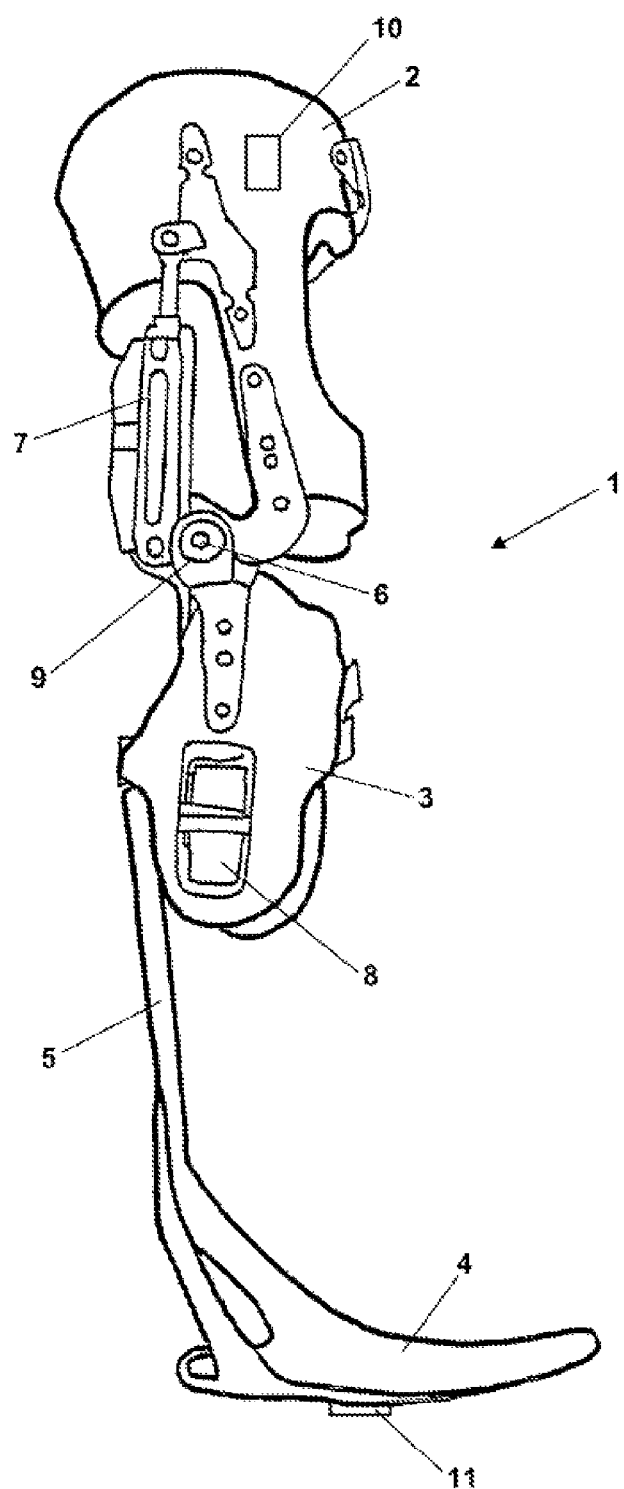
FIG. 1 shows an orthopedic device according to the invention in the form of a knee-ankle-foot orthosis.

The orthopedic device 1 depicted schematically in a side view in FIG. 1 is a knee-ankle-foot orthosis. The orthopedic device 1 includes connection apparatuses 2 to 4 for connection to a thigh, a lower leg and a foot of the wearer thereof. A flexible connecting element 5 is arranged between the connection apparatus 3 for the lower leg and the connection apparatus 4 for the foot. A joint 6 is provided between the connection apparatus 2 for the thigh and the connection apparatus for the lower leg. Assigned to the joint 6 is an adjustable actuator 7, for example in the form of a damper with variable damping, which damps the relative movement of the connection apparatus 2 about the joint in relation to the connection apparatus 3. The actuator 7 is set by control signals from a control apparatus 8. Here, the control apparatus 8 takes account of signals from sensors 9 to 11, which are only indicated schematically in FIG. 1. The sensor 9 registers the knee angle about the joint 6. The sensor 10 registers the hip angle of the connection apparatus 2 in relation to the vertical; and the sensor 11 registers the floor contact or a floor contact force. It is also possible for provision to be made for even more sensors at the orthopedic device 1 in order to register further movement parameters at the orthopedic device 1 or else state parameters of the orthopedic device 1, the surroundings thereof or the wearer thereof. Likewise, it is possible to provide further actuators—both passive ones, such as the actuator 7 embodied as a damper here, and active ones.

Figure 2:
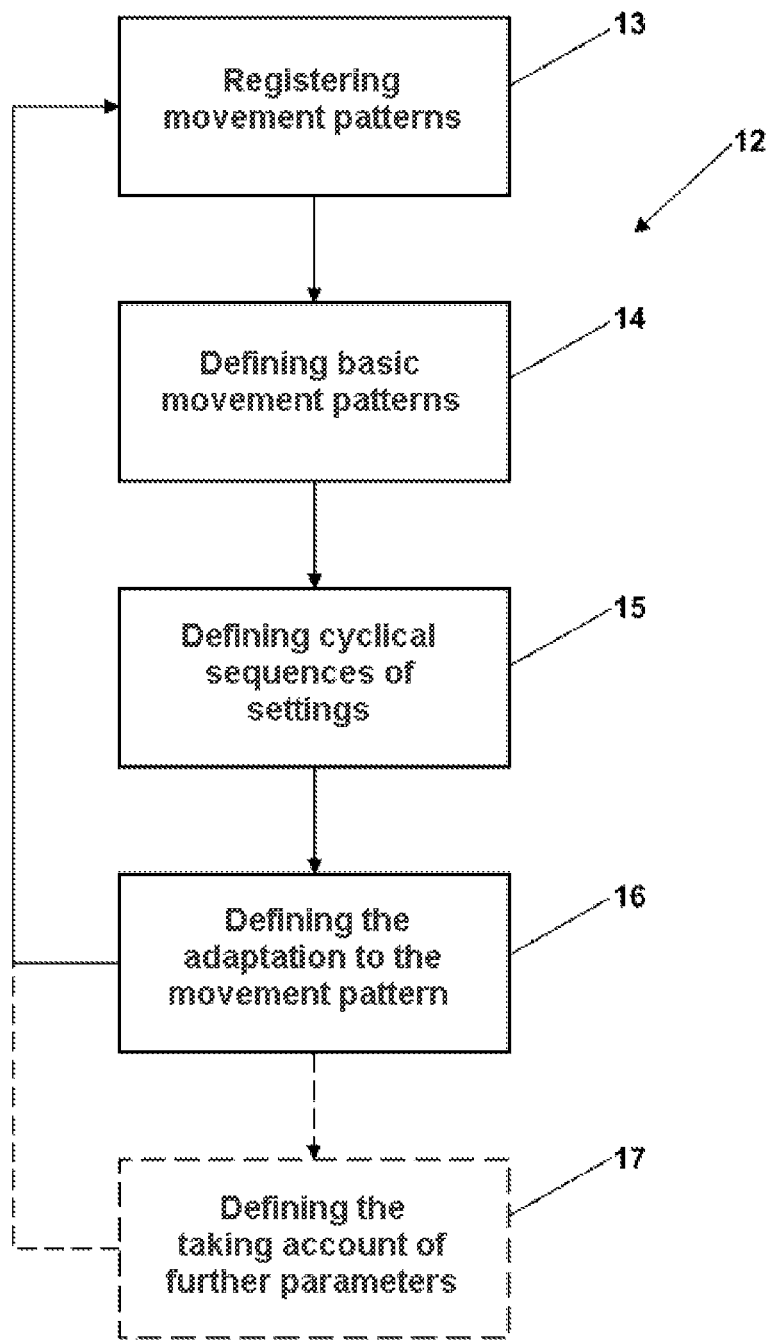
FIG. 2 is a flowchart relating to the setup of an orthopedic device according to the invention.

In order to prepare the control apparatus 8 of the orthopedic device 1 in accordance with FIG. 1 for the use of the orthopedic device 1 by a wearer (not depicted here), a setup 12 as sketched in FIG. 2 is to be carried out. In a first step 13, the movements of the wearer of the orthopedic device are observed and sequences of actual values of the movement parameters, which are acquired by the sensors 9 to 11 in accordance with FIG. 1, are registered. Here, the sequences of the actual values are assigned to specific movement patterns, such as e.g. walking in the plane or climbing stairs. The characteristic functional relationships for each of these movement patterns are established on the basis of functional relationships of the sequences of the actual values of the various movement parameters, and hence the movement patterns which respectively correspond to a plurality of movement patterns only differing e.g. in terms of the step speed are defined in step 14. Then, ideal settings of the actuator over each cycle of the respective movement pattern are defined in step 15 for these different movement patterns. This is brought about by virtue of respectively setting a sequence of intended values for setting the actuator. This is followed in step 16 by the definition as to how the respective sequence of the intended values is matched in terms of time to the actual values of the movement parameters. By way of example, this includes coupling to the sequence of the actual values of one of the movement parameters or a point-by-point synchronization with such actual values. In an optional step 17, it is then still possible to set the taking account of further parameters when generating the control signals at the actuator on the basis of the sequences of the intended values. By way of example, this includes adapting the respective sequence of the intended values as a function of the signal of an additional muscle tension sensor at the orthopedic apparatus, as a function of the surrounding temperature or the like.

Figure 3:
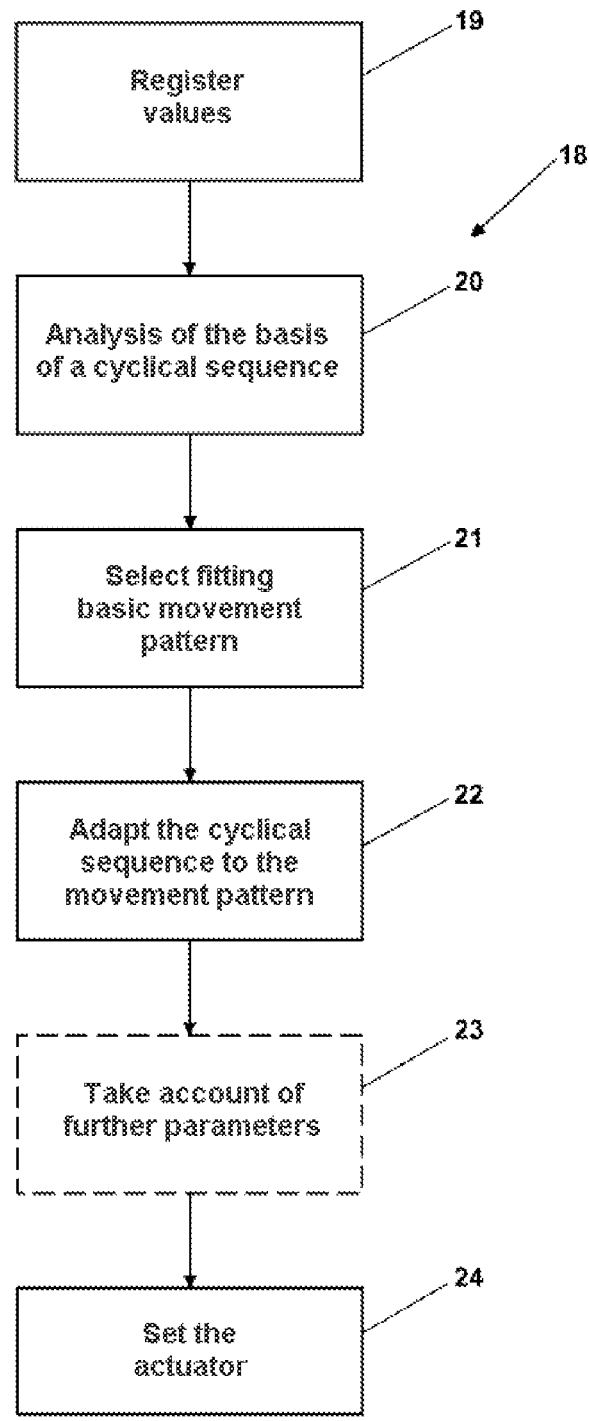
FIG. 3 is a flowchart relating to the operation of an orthopedic device according to the invention according to the method according to the invention.

The operation 18 of the orthopedic device, as sketched out in FIG. 3, starts with the actual values of the movement parameters being registered in step 19 using the sensors 9 to 11 in accordance with FIG. 1. In step 20, the sequences of these actual values are analyzed in the control apparatus 8 in respect of the functional relationship that is present between these. Then, the movement pattern as defined previously in step 14 in accordance with FIG. 2, whose functional relationship has the greatest correspondence to the current functional relationship, is selected in step 21 on the basis of the established functional relationship. In step 22, control signals for the actuator 7 in accordance with FIG. 1 are generated on the basis of the sequence of intended values which were assigned to the defined movement pattern selected thus in step 15 in accordance with FIG. 2. This is brought about in accordance with the definitions undertaken in step 16 of FIG. 2. Accordingly, it is possible, in step 23, to take account of further parameters for adapting the sequence of the intended values or the control signals generated therefrom in accordance with the definitions in step 17 of FIG. 2. Ultimately, the actuator 7 in accordance with FIG. 1 is set in step 24 using the control signals. The steps shown in FIG. 3 are performed in a continuously repeating manner and, in practice, do not proceed in such a way that there is only a block-by-block processing of whole sequences of actual values or intended values. Rather, the control signals fitting to determined actual values of the movement parameters are output as quickly as possible to the 7 in accordance with FIG. 1. In particular, this means that a control signal, once it is generated on the basis of an intended value, is output immediately. Accordingly, it is practically impossible to separate steps 22 to 24.

By taking account of the functional relationships of the movement parameters and the fitting movement patterns established therefrom, the method according to the invention can already set the actuator in a suitable manner for the respective next point in time since the potential deviation of the current actual values of the movement parameters deviates at best minimally from the values to be expected on the basis of selected movement pattern provided that no movement error is present. Even in the case of a change in the movement pattern, the physical inertia of the lower limb, to which the orthopedic device is connected, is at least just as large as the inertia with which the method according to the invention identifies a deviation from the previous movement pattern. If the transition to a different movement pattern is identified as a result of current deviations, the method according to the invention immediately seeks for the defined movement pattern which now has the best fit, wherein an early selection of such a movement pattern can initially also only be in the provisional manner until the selection is confirmed to be correct or incorrect. In the latter case, the initially selected movement pattern is replaced by a better fitting one.

By contrast, in the case of a movement error, which is generally defined by the previous functional relationship between the actual values of the movement parameters no longer existing but, at the same time, there also being indications for there not being a new functional relationship corresponding to a different defined movement pattern, the actuation of the actuator 7 in accordance with FIG. 1 is set to a fall-back value. From the fall-back value, the control apparatus returns to the actuation of the actuator on the basis of the sequence of intended values belonging to the movement pattern previously considered to have the best fit as soon as the actual values of the movement parameters return to the range of the previous functional relationship thereof. By way of example, the wearer of the orthopedic device 1 in accordance with FIG. 1 is thus assisted in an expedient manner if he has to overcome an instance of tripping or stumbling.

Figure 4:
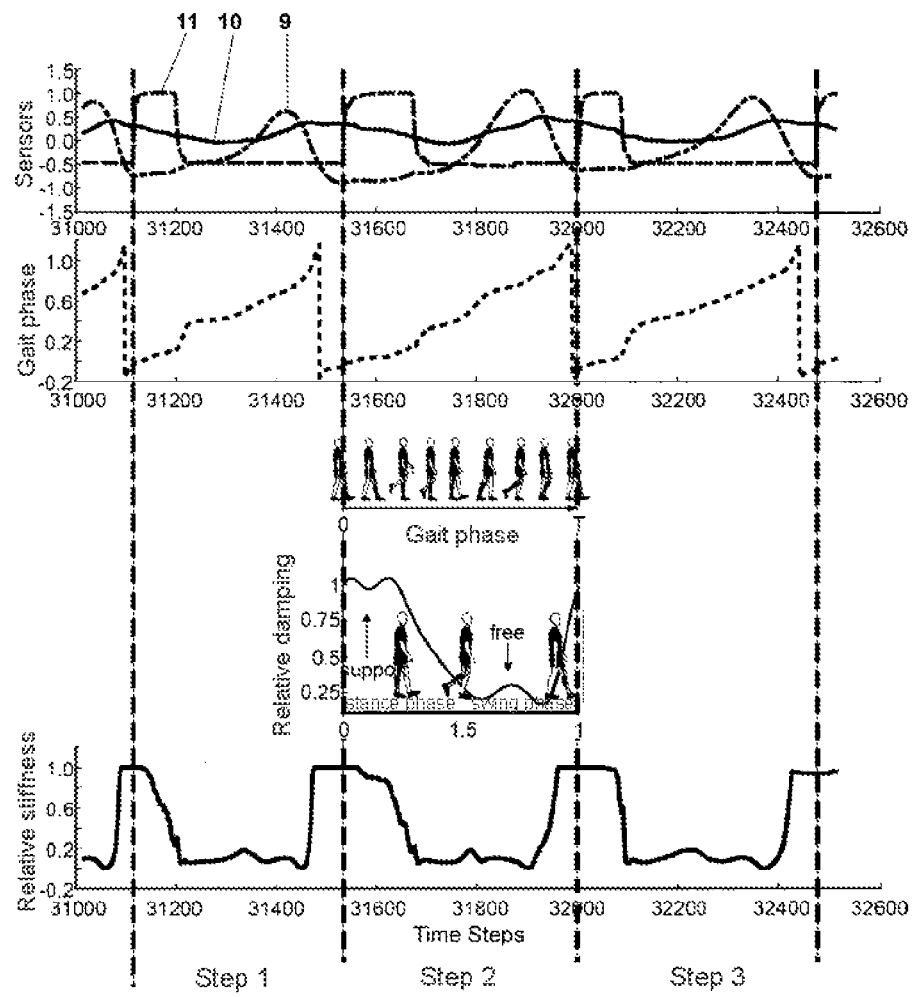
FIG. 4 shows, for an unchanging movement pattern, a plot of various movement parameters (very top), a gait phase (top) and the relative stiffness of an actuator of the orthosis, set according to the invention, in accordance with FIG. 1 (bottom) over time in "time steps"

At the very top, FIG. 4 shows, for a fixed movement pattern, the associated actual values of the movement parameters that are registered by the sensors 9 to 11 in accordance with FIG. 1. The actual values of the knee angle, which is registered by the sensor 9, are reproduced by a line consisting of dashes of different lengths. The actual values of the hip angle, which is registered by the sensor 10, are reproduced by a solid line, and the floor contact, which is registered by the sensor 11, is reproduced by a line consisting of dashes of equal length. The actual values show cyclical sequences, wherein each cycle corresponds to one step. Within each cycle, the sequences of the actual values of the hip angle and of the knee angle have an unchanging functional relationship, i.e. the sequences can be mapped onto one another by means of a mathematical function. This functional relationship is characteristic for the movement pattern present. Moreover, the progress of the gait phase can be deduced from the progress of this function; said gait phase is depicted at the top of FIG. 4 by way of a line consisting of short dashes and found below the values of the sensors. Then, the relative damping of the actuator 7 in accordance with FIG. 1 is set as a function of this gait phase. That is to say, the sequence of intended values, belonging to the movement pattern, for setting the actuator is used in phase with the gait phase for transmitting control signals to the actuator. As a result of this, the relative stiffness of the actuator 7, depicted at the bottom of FIG. 4 by a solid line, and hence of the joint 6 in accordance with FIG. 1, is set. These settings are in particular matched to the partial phases of the gait phase depicted at the bottom of FIG. 4, i.e. the standing phase ("stance phase") and the swing phase ("swing phase"). While the joint 6 in accordance with FIG. 1 is stiffer during the standing phase for assisting the wearer ("support"), it allows free swinging of the lower leg during the swing phase ("free").

Figure 5:
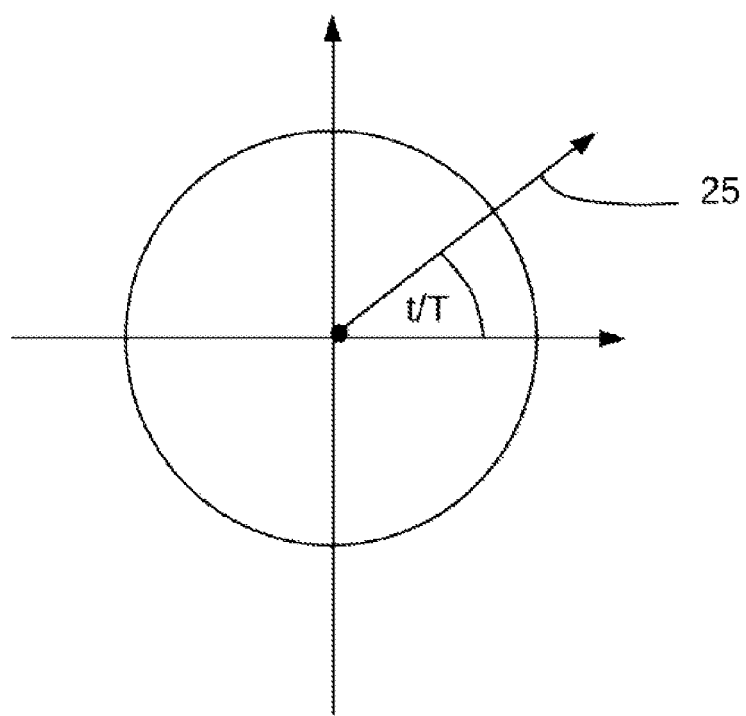
FIG. 5 shows a plot of two movement parameters as a trigonometric function.

FIG. 5 sketches a plot of the knee angle (horizontal) and of the hip angle (vertical) as a trigonometric function against the gait phase t/T, where T is a step duration. In principle, such a plot as a trigonometric function is also possible directly as a result of the phase offset between the knee angle and the hip angle. However, here, the knee angle and the hip angle are not plotted directly, but rather corresponding outputs of an artificial neural network, into which the time of the floor contact registered by the sensor 11 is input in addition to the knee angle and the hip angle. At least scaling of the knee angle and of the hip angle and phase tuning are expedient. The simultaneous actual values of the two angles reproduce the position of the phase vector 25 and therefore directly indicate the progress of the gait phase. This renders it possible to couple the sequence of the intended values for setting the actuator to the trigonometric function depicted in FIG. 5 in order to achieve an ideal synchronization of this sequence with the progress of the gait phase. Moreover, the representation as a trigonometric function in accordance with FIG. 5 directly shows the functional relationship between the knee angle and the hip angle. A comparison of the current functional relationship between these movement parameters and the functional relationships of defined movement patterns can also be brought about directly by way of the appropriate trigonometric functions and the deviations thereof from one another. The definition of the various movement patterns is likewise simplified by visualizing the functional relationship in the trigonometric function.

The invention claimed is:

1. A method for controlling an actuator of an orthopedic device including connection apparatuses to a lower limb, comprising the following steps carried out in a continuously repeating manner:
   registering actual values of at least two movement parameters of the orthopedic device using at least two sensors;
   comparing the registered actual values with defined movement patterns;
   selecting which of the defined movement patterns best fits the registered actual values; and
   generating control signals for the actuator using a sequence of intended values defined for a best-fitting of the selected defined movement patterns;
   wherein comparing the registered actual values with the defined movement patterns comprises:
   establishing a functional relationship between a sequence of the actual values of one of the at least two movement parameters and a sequence of the actual values of another one of the at least two movement parameters; and
   comparing the functional relationship with functional relationships in the defined movement patterns.

2. The method as claimed in claim 1, wherein a function is established during the step of establishing the functional relationship, and the function maps the sequence of the actual values of the one of the at least two movement parameters onto the sequence of the actual values of the another one of the at least two movement parameters.

3. The method as claimed in claim 2, wherein the function is represented by a trigonometric function in the step of establishing the functional relationship.

4. The method as claimed in claim 1, wherein the at least two sensors comprise at least one angle sensor.

5. The method as claimed in claim 1, wherein the at least two movement parameters are a hip angle and a knee angle.

6. The method as claimed in claim 1, wherein the sequence of the intended values is output as a function of the sequence of the actual values of at least one of the at least two movement parameters in the step of generating control signals for the actuator.

7. The method as claimed in claim 1, wherein the sequence of the intended values is synchronized on the basis of a signal from a further sensor.

8. The method as claimed in claim 7, wherein the further sensor is a foot or heel pressure sensor.

9. The method as claimed in claim 1, wherein a deviation of the actual values of the one of the at least two movement parameters from expected values, the expected values are predetermined by the actual values of the another one of the at least two movement parameters and a most recently established functional relationship between the sequences of the actual values of the at least two movement parameters, is classified as a movement error when at least one of:
the deviation has a duration below a predetermined duration limit, or
the actual values of the one of the at least two movement parameters during the deviation do not fit to any one of the defined movement patterns within a predetermined error limit.

10. The method as claimed in claim 9, wherein when the deviation is classified as the movement error, the control signals for the actuator are once again generated using the sequence of intended values defined for a most recent best-fitting movement pattern as soon as the actual values of the one of the at least two movement parameters once again correspond to the expected values.

11. The method as claimed in claim 9, wherein the control signals for the actuator are set to a predetermined fall-back value during the deviation classified as the movement error.

12. The method as claimed in claim 1, wherein the defined movement patterns are defined individually for a wearer of the orthopedic device.

13. The method as claimed in claim 1, wherein definitions of the defined movement patterns are updated on the basis of functional relationships assigned thereto.

14. The method as claimed in claim 1, wherein at least two movement patterns are defined.

15. The method as claimed in claim 1, wherein the sequence of intended values for the defined movement patterns are defined individually for a wearer of the orthopedic device.

16. The method as claimed in claim 1, wherein the sequence of intended values defined for the best-fitting of the selected defined movement patterns is adapted taking into account at least one of:
a history of the actual values of at least one of the movement parameters, or
a history of the functional relationship between the sequences of the actual values of the at least two movement parameters.

17. The method as claimed in claim 1, wherein at least one of at least one state value of the lower limb and at least one surrounding state value is registered by at least one state sensor, and the sequence of intended values defined for the best-fitting of the selected defined movement patterns is adapted taking into account the registered at least one of at least one state value and at least one surrounding state value.

18. An orthopedic device, comprising:
connection apparatuses to a lower limb;
an adjustable actuator;
at least two sensors which continuously register actual values of at least two movement parameters of the orthopedic device; and
a control apparatus which analyzes the registered values and sets the adjustable actuator using control signals;
wherein the control apparatus carries out the following steps in a continuously repeated manner:
registering the actual values of at least two movement parameters of the orthopedic device using the at least two sensors;
comparing the registered actual values with defined movement patterns;
selecting which of the defined movement patterns best fits the registered actual values; and
generating the control signals for the adjustable actuator using a sequence of intended values defined for a best-fitting of the selected defined movement patterns;
wherein comparing the registered actual values with the defined movement patterns comprises:
establishing a functional relationship between a sequence of the actual values of one of the at least two movement parameters and a sequence of the actual values of another one of the at least two movement parameters; and
comparing the functional relationship with functional relationships in the defined movement patterns.

19. The orthopedic device as claimed in claim 18, wherein the at least two movement parameters are a hip angle and a knee angle.

20. The orthopedic device as claimed in claim 18, wherein the orthopedic device further includes at least one of a foot or heel pressure sensor or a state sensor.

21. A method for controlling at least one adjustable actuator of an orthopedic device, comprising:
registering actual values of at least two movement parameters of the orthopedic device using at least two sensors;
comparing the registered actual values with defined movement patterns and selecting the defined movement patterns which most closely match the registered actual values, wherein comparing the registered actual values with the defined movement patterns comprises:
establishing a functional relationship between a sequence of the actual values of one of the at least two movement parameters and a sequence of the actual values of another one of the at least two movement parameters;
comparing the functional relationship with functional relationships in the defined movement patterns in order to select which of the defined movement patterns best fit the registered actual values;
generating control signals for the at least one adjustable actuator using a sequence of intended values defined for the selected defined movement patterns.

* * * * *